United States Patent [19]

Cerami

[11] Patent Number: 4,462,989

[45] Date of Patent: * Jul. 31, 1984

[54] METHOD AND AGENTS FOR ARRESTING INFECTION

[75] Inventor: Anthony Cerami, Flanders, N.J.

[73] Assignee: Evreka, Inc., Bergenfield, N.J.

[ * ] Notice: The portion of the term of this patent subsequent to Sep. 20, 2000 has been disclaimed.

[21] Appl. No.: 374,580

[22] Filed: May 3, 1982

Related U.S. Application Data

[63] Continuation-in-part of Ser. No. 260,144, May 4, 1981, Pat. No. 4,405,606.

[51] Int. Cl.³ .............................................. A61K 37/00
[52] U.S. Cl. ..................................................... 424/177
[58] Field of Search ......................................... 424/177

[56] References Cited

U.S. PATENT DOCUMENTS

| | | | |
|---|---|---|---|
| 4,061,735 | 12/1977 | Funakoshi et al. | 424/177 |
| 4,113,853 | 9/1978 | Funakoshi et al. | 424/177 |
| 4,137,307 | 1/1979 | Funakoshi et al. | 424/177 |

OTHER PUBLICATIONS

Graziano, J. H. et al., "The Identification of 2,3-Dihydroxybenzoic Acid as a Potentially Useful Iron-Chelating Drug" J. Pharmacol. Exp. Therap. 190:570-575, 1974.

White, G. P. et al., "The Effect of Chelating Agents on Iron Mobilization in Chang Cell Cultures" Blood 48:923-929, 1976.

Grady, R. W. et al., "Development of New Iron--Chelating Drugs", Part II, J. Pharmacol. & Exper. Therap., 205:757-765, 1978.

Grady, R. W. et al., "The Current Status of Iron Chelation", Ann. Rev. Med. Chem. 13:219-226, 1978.

Hershko, C. et al., "Mechanism of Iron Chelation in the Hypertransfused Rat: Definition of Two Alternative Pathways of Iron Metabolism", J. Lab. Clin. Med. 92:144-151, 1978.

Bhargava, K. K. et al., "New Compounds: $N^1$, $N^8$-bis-(2,3-dihydroxybenzoly)-Spermidine and Several Analogues-Potential Iron-Chelating Drugs", J. Pharm. Sci. 69-986-989, 1980.

Jones, R. L. et al., "A Low Molecular Weight Iron Binding Factor from Mammalian Tissue which Potentiates Bacterial Growth in Vitro and in Vivo", J. of Exp. Med. 151:148-428, 1980.

Pagano, M. et al., "Kinetic Study of the Interaction Between Rat Haptoglobin and Rat Liver Cathepsin B", Can. J. Biochem. 58:410-417, (1980).

Eaton, J. et al., "Haptoglobin: A Natural Bacteriostat", Science, 215:691-693 (1982).

Eaton, J. W. et al., "Haptoglobin Prevents Lethal Hemoglobin-Driven Bacterial Peritonitis" (abstract submitted to American Society of Hemotology on Sep. 24, 1981).

(List continued on next page.)

Primary Examiner—Delbert R. Phillips
Assistant Examiner—F. T. Moezie
Attorney, Agent, or Firm—David A. Jackson; Daniel H. Bobis

[57] ABSTRACT

A method and associated agents for the arrest of infections resulting from organism growth in contact with an iron-containing body fluid, comprising administering an agent capable of immobilizing the body fluid so that the iron it contains is nutritionally unavailable for the organism. In the instance where the body fluid is blood, the agent may be administered in amounts effective to bind all of the available red blood cells or hemoglobin, to prevent breakdown of either and consequent release of iron to the organism.

The agents preferably include materials capable of binding red blood cells and iron, such as haptoglobin, colloidal silica, anion exchange resins and mixtures thereof. Preferably, colloidal silica is used either alone or in a composite with a polyolefin elastomer such as polyisobutylene.

The agents may be coated on carriers or substrates, such as gauze pads, tampons and the like, and may be thus utilized topically, as well as intraperitoneally.

20 Claims, 2 Drawing Figures

OTHER PUBLICATIONS

D. Falkenhagen et al., "Serum Complement and Protein Metabolism in Chronic Dialysis Patients", Int. J. Art. Org. 2(2) at 65–68 (1979).

F. Wesenberg, "Characterization of Heat Eluates of Human Malignant Tissues", Acta Path. Microbiol Scand., Sect. C, 87 at 301–306 (1979).

F. Archibald et al., "Removal of Iron from Human Transferring by *Neisseria Meningitidis*", Fems Microbiol. Letters 6 at 159–162 (1979).

G. Calver et al., "Inhibition of the Growth of *Neisseria Meningitidis* by Reduced Ferritin and Other Iron-Binding Agents", Inf. and Imm. 25(3) at 880–890 (1979).

J. Davis et al., "A Possible Toxic Factor in Abdominal Injury", J. Trauma, 2:291–300 (1962).

Litwin et al., "Synergistic Toxicity of Gram-Negative Bacteria and Free Colloidal Hemoglobin", Ann. Surg., 157(4):485–493 (1963).

T. Hau et al., Surgery, 86(5):588–592 (1980).

J. Fletcher, "The Effect of Iron and Transferrin on the Killing of *Escherichia coli* in Fresh Serum", Immunol., 20:493–500 (1971).

A. Trippestad et al., "The Role of Hemoglobin for the Lethal Effect of Intestinal Strangulation Fluid", J. Surg. Res., 10(10):465–470 (1970).

J. J. Bullen et al., "The Effect of Iron Compounds on the Virulence of *Escherichia coli* for Guinea-Pigs", Immunol., 15:581–588 (1968).

G. H. Bornside et al., "Hemoglobin and *Escherichia coli*, a Lethal Intraperitoneal Combination", J. Bact., 95(5):1567–1571 (1968).

T. Hau et al., Surgery, 83(2):223–229 (1978).

J. T. Lee, Jr. et al., Surgery, 86(1):41–48 (1979).

J. H. Davis et al., "A Toxic Factor in Abdominal Injury II: The Role of the Red Cell Component", J. Trauma, 4:84–90 (1964).

J. Eisenlauer et al., "Stability of Colloidal Silica (Aerosil) Hydrosols, I. Preparation and Characterization of Silica (Aerosil) Hydrosols", J. Colloid Interface Sci., 74(1):108–119 (1980).

J. Eisenlauer et al., "Stability of Colloidal Silica (Aerosil) Hydrosols, II Influence of the pH Value and the Adsorption of Polyethylene Glycols", J. Colloid and Interface Sci., 74(1):120–135 (1980).

B. E. Hallaway et al., "Changes in Conformation and Function of Hemoglobin and Myoglobin Induced by Adsorption to Silica", Biochem. Biophys. Res. Comm., 86(3):689–696 (1979).

METHOD AND AGENTS FOR ARRESTING INFECTION

CROSS REFERENCE TO RELATED APPLICATION

The present application is a continuation-in-part of copending application Ser. No. 260,144, filed May 4, 1981, now U.S. Pat. No. 4,405,606 issued Sept. 20, 1983 by the inventor herein.

BACKGROUND OF THE INVENTION

1. Field of the Invention

The present invention relates to animal tissue infections, and particularly to methods and agents useful in their control and inhibition.

2. Description of the Prior Art

Bacterial infections, and particularly those that develop at the sight of tissue trauma, or at any location where bleeding takes place have long been of concern, and, as such, the subject of investigation, for the purposes of developing procedures for their control. Thus, whether topical or peritoneal in location, these bacterial infections frequently become fulminating in nature and can, in some instances result in death.

Prior art efforts to control the spread of infection, have involved the removal of the unwanted blood from the area of the trauma, or, in the instance of peritoneal surgery, irrigation of the area with a washing fluid containing one or more selected antibiotics. These measures have proved to be inadequate, however, as infection proceeds at too rapid a rate.

Similar difficulties in the area of personal hygiene, have been found to result when unwanted blood is present. Specifically, certain bacteria that develop during the menstrual cycle, cause discomfort and frequently result in the evolution of noxious odors. In some instances, however, far more dangerous consequences develop, as in the instance of the well known "toxic shock syndrome", that had been reported with respect to the use of a particular brand of tampon device. In such instance, the bacteria S. aureus, for example, was offered a particularly conducive environment, and rapid infection developed, despite the periodic removal that is characteristic of tampon use during the menstrual cycle.

In my previous application Ser. No. 260,144, a relationship between the infectious growth of bacteria, and the presence at the location of such growth, of free blood or hemoglobin was noted. A method was proposed for the arrest of infection, that made use of the complex-forming protein haptoglobin, and, in particular, comprised a method whereby haptoglobin was administered in exogenous form to the place where the trauma and, therefore, the free blood or hemoglobin is present. The present application seeks to expand upon this concept by proposing additional agents and methods of their use.

SUMMARY OF THE INVENTION

In accordance with the present invention, a method for arresting organism-promoted animal tissue infection in the presence of iron-containing body fluid, comprises administering an agent capable of immobilizing the body fluid to make the iron nutritionally unavailable to the infection-promoting organism. The present method may be used to make the red blood cells or the hemoglobin fraction of free blood in the vicinity of a tissue trauma unavailable by infection-promoting bacteria, so that the bacteria cannot abstract the iron necessary for their growth. A wide variety of bacteria thrive on available iron, and range in activity from lethal, infection-causing varieties, to those that cause the evolution of undesirable odor during their life cycle.

Agents useful in the present invention include those materials that are capable of forming an immobilized complex with red blood cells as well as with hemoglobin and may be selected from the group consisting of antibodies against red blood cells, antibodies against hemoglobin, anionic exchange resins, colloidal silica, complex-binding proteins for either or both red blood cells or hemoglobin, and mixtures thereof. The agents may be utilized alone or in fluids, or may be disposed as coatings on appliances such as bandages, gauze pads, surgical sponges, sanitary napkins, tampons and the like.

In a preferred embodiment, the agents of the present invention are selected from colloidal silica, either alone or in combination with a supporting matrix, anionic exchange resins including cellulose-based resins, resins capable of binding to sulfhydryl groups, plant lectins capable of binding with sugar, and exogenous haptoglobin. Preferably, the agent utilized comprises colloidal silica suspended in a matrix of polyisobutylene.

In the instance where the agent is administered to a peritoneal trauma, a sterile solution containing the agent may be prepared in a concentration that may range from about 1.0 to about 100 mg./ml. Administration may be either by direct dosage or by incorporation into conventional irrigation fluids. In the instance where topical treatments are contemplated, the agents must be disposed on the topical applicator or carrier in a manner such that the agent is available for surface contact with the blood or hemoglobin. Thus, for example, efforts to impregnate the agent into fibers and the like have been tried but with no success.

The various agents useful in the present invention are widely available and are inexpensive to recover and utilize, so that the present method may be widely practiced.

Accordingly, it is a principal object of the present invention to provide a method for arresting bacterial infections that develop in the presence of body fluids offering available iron.

It is a further object of the present invention to provide a method as aforesaid that operates in rapid and complete fashion.

It is a yet further object of the present invention to provide a method as aforesaid that may utilize a variety of agents, in both topical and intraperitoneal application.

It is a still further object of the present invention to provide agents and products carrying these agents, for use in arresting bacterial infections.

It is a still further object of the present invention to prepare agents and products as aforesaid which are inexpensive to prepare and simple to use.

Other objects and advantages will become apparent to those skilled in the art from a consideration of the ensuing description which proceeds with reference to the following illustrative drawings.

DETAILED DESCRIPTION

Figure 1:
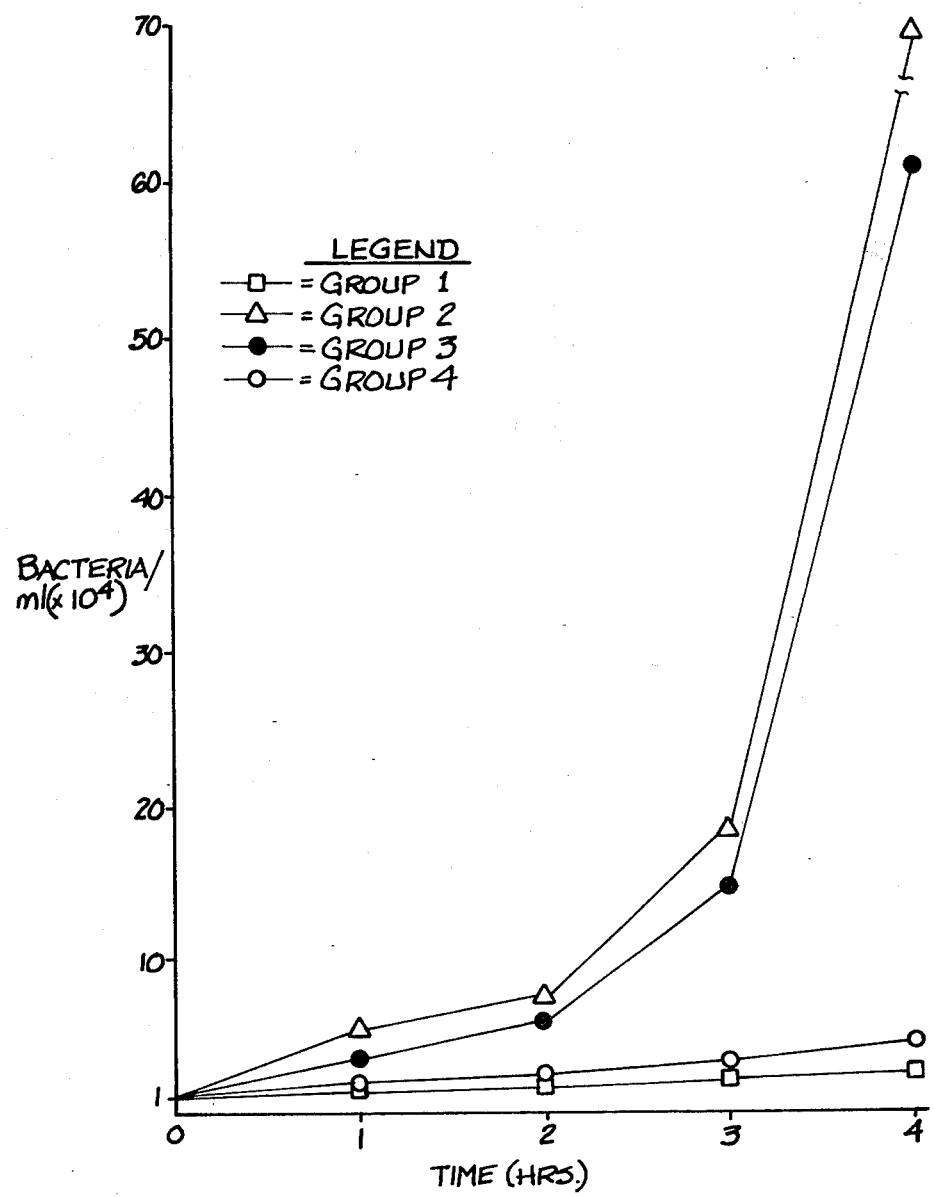
FIGS. 1 and 2 graphically represent the results of in vitro testing of the method of the present invention, utilizing colloidal silica as the binding agent.

In accordance with the present invention, the method for arresting tissue infection in the presence of a body fluid containing iron accessible to the infection-promoting organisms, comprises administering to the locus of infection an agent capable of immobilizing the body fluid so that the iron is made nutritionally unavailable to the organisms. In the instance where the body fluid is blood, the agent is administered in an amount sufficient to immobilize either the red blood cells or the hemoglobin present in the blood adjacent the organisms. The amount of the agent administered will therefore be proportional to the amount of the component of the blood sought to be immobilized.

Agents useful in the immobilization of blood may be divided into two categories, depending upon the component of the blood for which immobilization is desired. In the instance where it is desired to immobilize the red blood cell, the agents may comprise antibodies against the red blood cell, colloidal silica, anionic exchange resins, plant lectins capable of binding sugars, such as Concanavalin A, and other materials known to aggregate red blood cells. In the instance where the component to be immobilized is hemoglobin, the agent may be selected from antibodies against hemoglobin, colloidal silica, anionic exchange resins, complexing proteins such as haptoglobin, and other materials having a known capability of binding hemoglobin.

As discussed earlier, work previously done on this subject, has determined that bacterial organisms were capable of digesting the red blood cell and the hemoglobin, to abstract and adsorb the contained iron, to make it available for nutrition and growth. In particular, Eaton et al., "Haptoglobin: A Natural Bacteriostat", SCIENCE, 215:691–692 (1982), summarized work performed on behalf and under the direction of the present inventor, and included in earlier Ser. No. 260,144, and restated the observations by earlier workers that the available iron abstracted from blood present in a wound, gave the bacteria sufficient nutrition to achieve rapid replication, so that the natural body defenses were inadequate to control the resulting fulminating infection. The disclosure of the Eaton et al. article is incorporated herein by reference.

The present invention expands the concept set forth in the earlier application, by disclosing a method whereby a variety of agents may be utilized both peritoneally and topically, in amounts sufficient to bind either available red blood cells or available hemoglobin, and prevent either of the two from being broken down by the undesired bacteria for the purpose of abstracting the iron contained therein.

Under normal conditions, the iron-containing fractions of blood are maintained secure against breakdown by association with certain complexing proteins. In particular, the fraction hemoglobin is secured by association with the protein haptoglobin, while the heme fraction is bound by the protein hemopexin, and iron occurring as iron salts is bound by the protein transferrin. Each of the foregoing binding or complexing proteins, however, is present in relatively small amounts under normal circumstances. Increases of the levels of these proteins can occur gradually, in response to the onset of certain internal pathological conditions; however, the body is not equipped to rapidly provide the relatively massive amounts of these proteins necessary to maintain iron in the unavailable sequestered state, such as in the instance where tissue trauma takes place and the blood is released from the vascular system into the peritoneum and thereby into contact with infection-promoting bacteria. Similarly, in the instance where natural release of blood takes place, or in the instance of topical abrasions and cuts, the quantity of blood released is frequently far in excess of the capability of these natural complexing agents. The difficulty engendered by this problem is apparent from a consideration that the red blood cells derived from 1 milliliter of blood can yield up to 150 milligrams of hemoglobin after red cell breakdown, a value that far exceeds the capacity of any haptoglobin normally present in that quantity of blood.

Accordingly, the present method proposes to administer relatively large amounts of agents capable of binding either the red blood cells or the hemoglobin component of the blood released in any of these situations. Thus, in the instance of tissue trauma, due to surgical procedures or the like, a sterile solution containing the agent of the present invention may be directly administered by injection or otherwise, or may be incorporated in an irrigation fluid that is utilized to wash body wound areas. Additionally, the agent may be affixed to a surgical sponge which may then be utilized in contact with the blood. In the instance where the solutions of the agent are utilized, they may be prepared to concentrations of up to about 100 milligrams per milliliter, and preferably from about 1.0 to about 100 milligrams per milliliter. Naturally, these quantities are illustrative only, and may vary in accordance with the present invention.

In the instance where the agent is utilized for topical application, it may be disposed on various topical appliances, such as bandages and gauze pads, as well as sanitary and catamenial devices such as tampons. For example, in this latter instance, the agent may be disposed within a container in a tampon or within the pores of the absorbent material, as disclosed, respectively, in U.S. Pat. No. 3,842,166 to Bucalo and U.S. Pat. No. 3,850,160 to Denson, cited herein as exemplary only.

In the instance where the present agents comprise colloidal silica, a particular form of colloidal silica is contemplated which is identified commercially as "Cab-O-Sil®". This product is manufactured by the Cabot Corporation, Boston, Massachusetts and is generally known for its use as an anti-agglomerative in various compositions, and as a general adsorbent. "Cab-O-Sil®" comprises colloidal, submicroscopic, pyrogenic silica prepared in a hot, gaseous environment by a vapor phase flame hydrolysis, at high temperature (around 1100° C.) of a silicon compound, such as silicon tetrachloride. It is distinct from silica gel obtained by precipitation of silicic acid from an aqueous silicate solution, and hardening of the precipitate. Silica gel, thus formed is internally porous, whereas "Cab-O-Sil®" has an enormous external surface area and no internal porosity.

"Cab-O-Sil®" contains no water-soluble inorganic salts. It is of high chemical purity, low water content and has a high degree of particle separation. The properties and composition of a grade of "Cab-O-Sil®" are listed as follows:

Silica Content (moisture free)—99.0–99.7%
Free Moisture (105° C.)—0.2–1.5%
Ignition loss at 1000° C. (excluding moisture)—0.2–1.0%
CaO,MgO—0.00%
$Fe_2O_3 + Al_2O_3$—0.01%

Particle size range—0.015–0.020 micron
Surface area—175–200 sq. m./gm.
Specific gravity—2.1
Color—white
Refractive index—1.46
pH (4% aqueous dispersion)—3.5–4.2
Apparent bulk density—2.5–7.0 lbs./cu. ft.

A finer grade of "Cab-O-Sil ®" has the above characteristics but a particle size range of 0.007–0.010 micron, a surface area of substantially 325 sq. m./gm., and a refractive index of 1.46.

As mentioned earlier, this form of colloidal silica may be utilized alone in solution form as the agent. In the instance, however, where it is to be disposed either within or upon a carrier or substrate, it is preferably prepared in a composite particulate form with a polyolefinic elastomeric organic binder. In particular, food grade polyisobutylene may be utilized. In such instance, the colloidal silica is suspended in a dilute hydrocarbon solution of the elastomer, and the resulting suspension is spread on an appropriate surface and dried to form the flake-like particles of the composite.

In a preferred embodiment, the composite of the colloidal silica and the polyisobutylene is prepared in proportions of approximately 85% colloidal silica, 15% polyisobutylene, such proportions determined by weight of the composite. This material may then be affixed by conventional procedures to a variety of substrates for further use.

In the instance where certain tests of the colloidal silica were made, where the colloidal silica was incorporated within a variety of fibrous materials which were then tested in contact with blood and bacteria on an in vitro basis, the materials ranged from rayon filament, to rayon staple, and fibers of various sizes, prepared from silica, silicic acid and fiber glass. In each instance, the colloidal silica was found to be inactive at binding hemoglobin.

By contrast, the preparation of the colloidal silica-polyisobutylene composite offers the same activity as that of the colloidal silica alone, when disposed on, or within, a carrier or substrate.

Another class of agents that is useful both for hemoglobin and red blood cells comprises anionic exchange resins such as diethylaminoethylcellulose (DEAE-Cellulose), guanidoethylcellulose, diethyl(2-hydroxypropyl)aminoethyldextran (QAE-Sephadex), and resins capable of binding compounds having available sulfhydryl groups, such as polyethyleneimine. The number of suitable anionic exchangers is large, and the foregoing listing is merely exemplary.

Also as mentioned earlier, various complex proteins may be utilized as the agent, and thus are included the materials specified in my earlier application, already incorporated herein by reference. Thus, in addition to haptoglobin and transferrin, complex proteins such as the macromolecular binding materials known as plant lectins, may be utilized either in solution, or disposed on a substrate.

Lectins are known carbohydrate-binding proteins derived from plants and animals, having a wide variety of specificity. For example, Concanavalin A, a jack bean lectin, has specificity for α-D mannopyranose and α-D glucopyranose; soybean lectins show specificity for α and β-D-N-acetylgalactosamine and α-D-galactose units, while wheat germ lectin is specific for β-D-N-acetylglucosamine. Naturally, the specific complex-forming proteins selected and utilized will vary with the nature of the organisms to be inhibited, as well as the conditions in which the organisms are found.

Likewise, the agents of the present invention may be utilized individually or in mixtures, depending upon the environment in which use is contemplated. For example, one may combine a quantity of DEAE-Cellulose with "Cab-O-Sil ®" for use, for example, in the treatment of surgical wounds.

With respect to "Cab-O-Sil ®", the effective administration of this agent has been limited somewhat to instances where large amounts of a free monovalent anion such as chloride are absent from the locus of administration. In such instances, the preparation of the composite Cab-O-Sil ®-polyisobutylene particles appears to overcome this restriction, as such particles are capable of operating effectively even in the presence of physiological concentrations of chloride.

The method of the present invention, and the operation of the agents thereof, will be better understood from a consideration of the following examples, wherein amounts of materials expressed in percent, are intended to refer to percent by weight.

EXAMPLE I

A large amount of growth media was prepared having a low iron content. The growth media comprised 5 milliliter aliquot portions of heat-inactivated human serum. Media were prepared with variant additives, and thereafter equal quantities of the bacteria were added. The media were thereafter inoculated with equal quantities of the bacteria. Four primary groupings of inocula were developed as follows:

1. Group 1—The bacteria *E. coli* alone.
2. Group 2—*E. coli,* Ferric ammonium citrate (FAC) (amount of 45.3 μg), with or without 50 milligrams Cab-O-Sil ®.
3. Group 3—*E. coli* and a small amount of hemoglobin (2 milligrams).
4. Group 4—*E. coli,* hemoglobin as in Group 3, and Cab-O-Sil ® (50 milligrams).

In the instance where Cab-O-Sil ® and hemoglobin were both added, a pre-mixture of the two was made, so that the hemoglobin was initially adsorbed to the Cab-O-Sil ®, and the resulting adduct was then added to the growth medium.

After preparation, all samples were maintained at the same temperature, and were observed for a period of time ranging up to about 24 hours following inoculation. Hourly bacterial counts were made, and have been provided, as to the first 4 hours of observation, in FIG. 1.

The data from the respective groupings is identified by the corresponding graphical symbols set forth in the legend. The data points plotted in FIG. 1 represent the respective mean and standard deviation values determined from a comparison of 3 samples of each grouping observed and counted at the indicated time interval.

Referring to FIG. 1, the rate of growth of the bacteria *E. coli* alone can be seen to be relatively flat, so that the initial or lag phase of bacterial growth is apparent. By contrast the addition of either the Ferric ammonium citrate (Group 2) or the hemoglobin alone (Group 3) to the growth medium results in a dramatic acceleration in bacterial growth. It is also noteworthy that Cab-O-Sil ® when added to the Group 2 media, appeared to have no inhibitory effect upon bacterial growth, so that the availability of iron from this synthetic source was not controlled.

In Group 4, however, where both hemoglobin and Cab-O-Sil ® were added, the acceleration of bacterial growth evident with Groups 2 and 3 was absent and had apparently been neutralized. Thus, Group 4 exhibited a growth pattern similar in rate to that of Group 1, comprising the low-iron containing serum alone. The specificity of Cab-O-Sil ® is suggested by a comparison of Groups 2 and 4. While Cab-O-Sil ® appears to be ineffective against the synthetic iron-providing compound Ferric ammonium citrate, activity is present with respect to hemoglobin.

EXAMPLE II

Additional tests were conducted, similar in format to those described in Example I, above. Accordingly, similar growth media were prepared and were inoculated with E. coli in like fashion. Four primary groupings of additive inocula were developed as follows:
1. Group 1—The bacteria E. coli alone.
2. Group 2—E. coli and a small amount of hemoglobin (2 milligrams).
3. Group 3—E. coli and Cab-O-Sil ® (50 milligrams).
4. Group 4—E. coli, hemoglobin as in Group 2 and Cab-O-Sil ® as in Group 3.

Figure 2:
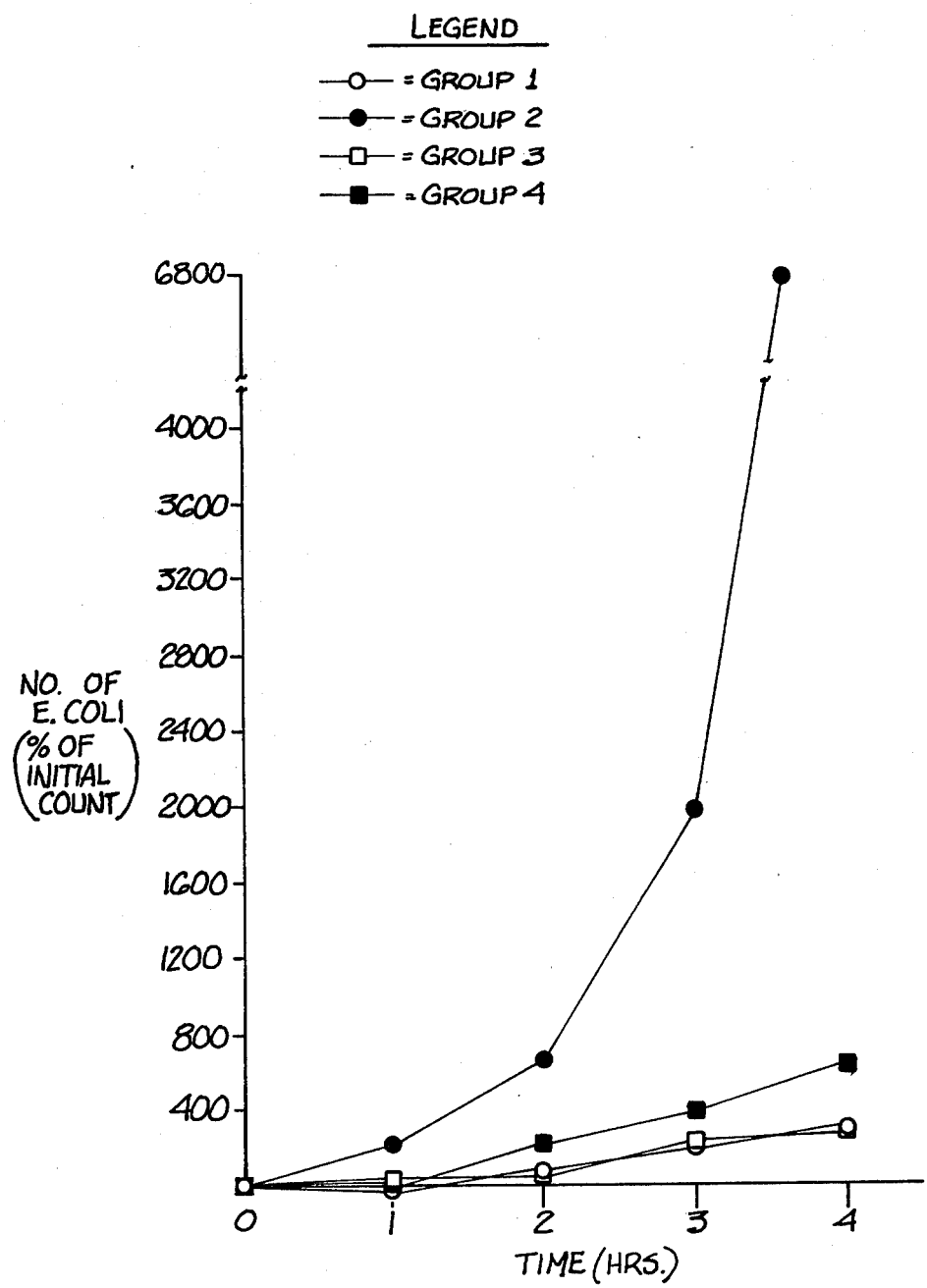

Similar conditions were observed, and the respective media were followed for approximately 24 hours, with the results of the first 4 hours of growth tabulated and set forth in FIG. 2.

In similar fashion to the results of FIG. 1, the media wherein the E. coli was present alone (Group 1) or was present in combination with Cab-O-Sil ®, the growth exhibited followed the expected lag phase pattern. By contrast, growth was greatly accelerated in the instance where hemoglobin was added (Group 2) but was inhibited in the instance where Cab-O-Sil ® was added to hemoglobin (Group 4). This last grouping exhibited a growth pattern comparable to that of Groups 1 and 3, where hemoglobin had not been added.

The results of these tests confirm the conclusions reached with respect to the tests depicted in FIG. 1, that Cab-O-Sil ® exhibits a specific effectiveness in the sequestration of hemoglobin.

EXAMPLE III

A specific preparation of a composite useful for coating or adsorption on solid substrates was prepared. A quantity of Cab-O-Sil ® Grade M-5 and a polyisobutylene identified as Oppanol ® Grade B-150 were combined in the ratio of 85% Cab-O-Sil ® to 15% polyisobutylene. A dilute hydrocarbon of Oppanol ® B-150 was prepared and the Cab-O-Sil ® was suspended therein. The suspension was thereafter cast on a flat surface and dried, and yielded a flake-like composite in which the Cab-O-Sil ® particles were bound to the polyisobutylene matrix.

Accordingly, the present invention includes coated articles useful to dispense the blood or hemoglobin-immobilizing agents. For example, fibrous materials such as rayon, cellulose fiber and others utilized in the preparation of products such as gauze pads, skin bandages and the like, may be impregnated or otherwise coated with the agents disposed in a solution or suspension, after which the resulting coating article may be appropriately dried to volatize off any undesired vehicle. In the instance where the suspension of Cab-O-Sil ® is prepared as set forth in Example III, above, the intended substrate may be dipped or otherwise coated by the liquid suspension prior to the evaporation of the solvent, so that the resulting particles or flakes may be fixed to the substrate when dry.

As mentioned earlier, the present invention possesses a broad spectrum of uses, going beyond the treatment of peritoneal infection. The present method and associated agents may extend to topical treatments and other personal hygiene instances where a fluid and a bacteria are in contact with each other, and where that fluid may contain a quantity of an iron-containing body fluid, such as blood.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

I claim:

1. A method for arresting infection in animals in the presence of a body fluid containing iron accessible to the organisms promoting said infection, comprising administering to said infection an exogenously derived agent capable of forming a complex with the iron in said body fluid, which complex is indigestible by said infection promoting organisms, to make said iron nutritionally unavailable to said organisms.

2. The method of claim 1 wherein said agent is selected from the group consisting of antibodies against red blood cells, antibodies against hemoglobin, plant lectins, anion exchange resins, colloidal silica, a composite of colloidal silica and a polyolefinic elastomer, resins capable of binding to sulfhydryl groups, and mixtures thereof.

3. The method of claim 2 wherein said agent is selected from the group consisting of colloidal silica, colloidal silica and a polyolefinic elastomer, cellulose-based anion exchange resins, polyethyleneimine, and mixtures thereof.

4. The method of claim 3 wherein said composite comprises a mixture of said colloidal silica and polyisobutylene.

5. The method of claim 4 wherein said composite comprises 85% colloidal silica and 15% polyisobutylene.

6. The method of claims 1, 2 or 5 wherein said agent is disposed in a sterile solution.

7. The method of claim 6 wherein said sterile solution contains from about 1.0 to about 100 mg./ml. of said agent.

8. The method of claims 1, 2 or 6 wherein said agent is added to an irrigation fluid utilized at the locus of a tissue wound.

9. The method of claim 4 wherein said agent is disposed in a sterile solution.

10. The method of claim 9 wherein said sterile solution contains from about 1.0 to about 100 mg./ml. of said agent.

11. The method of claim 9 wherein said agent is added to an irrigation fluid utilized at the locus of a tissue wound.

12. A composition for use in arresting bacterial infection in animals in the presence of a body fluid containing iron accessible to the bacteria promoting said infection, comprising an effective amount of an agent selected from the group consisting of antibodies against red blood cells, antibodies against hemoglobin, plant lectins, anion exchange resins, resins capable of binding to sulfhydryl groups, colloidal silica, a composite of colloidal silica and a polyolefinic elastomer, and mixtures thereof; and a pharmaceutically acceptable carrier.

13. The composition of claim 12 wherein said anion exchange resins comprise diethylaminoethylcellulose, guanidoethylcellulose, diethyl(2-hydroxypropyl)aminoethyl dextran, and compounds capable of binding sulfhydryl groups, and said composite comprises colloidal silica and polyisobutylene.

14. The composition of claim 13 wherein said agent comprises a mixture of diethylaminoethylcellulose and colloidal silica.

15. The composition of claim 13 wherein said agent comprises said composite alone.

16. The composition of either of claims 13 or 15 wherein said composite contains 85% colloidal silica and 15% polyisobutylene.

17. An appliance for use in arresting bacterial infection comprising an absorbent substrate having at least a portion of its effective surface area coated with the composition of claims 12 or 13.

18. An appliance for use in arresting bacterial infection comprising an absorbent substrate having at least a portion of its effective surface area coated with the composition of claim 16.

19. The appliance of claim 17 wherein said absorbent substate is selected from surgical sponges, bandages, gauze, sanitary napkins, and tampons.

20. The appliance of claim 18 wherein said absorbent substrate is selected from surgical sponges, bandages, gauze, sanitary napkins, and tampons.

* * * * *